(12) United States Patent
Kazakevich

(10) Patent No.: US 6,749,561 B2
(45) Date of Patent: Jun. 15, 2004

(54) AUTOFOCUSING ENDOSCOPIC SYSTEM

(75) Inventor: Yuri Kazakevich, Andover, MA (US)

(73) Assignee: Smith & Nephew, Inc., Andover, MA (US)

( * ) Notice: Subject to any disclaimer, the term of this patent is extended or adjusted under 35 U.S.C. 154(b) by 201 days.

(21) Appl. No.: 09/938,126

(22) Filed: Aug. 23, 2001

(65) Prior Publication Data

US 2003/0040659 A1 Feb. 27, 2003

(51) Int. Cl.[7] ............................... A61B 1/04; G02B 7/28
(52) U.S. Cl. .................. 600/167; 600/109; 600/921; 348/353
(58) Field of Search ............................ 600/167, 109, 600/921; 348/353, 354; 250/201.7, 201.2

(56) References Cited

U.S. PATENT DOCUMENTS

| | | | |
|---|---|---|---|
| 3,783,269 A | * | 1/1974 | McConnell .............. 250/201.7 |
| 4,593,322 A | * | 6/1986 | Abel ........................... 348/354 |
| 4,766,489 A | * | 8/1988 | Kato ............................. 348/70 |
| 4,843,472 A | * | 6/1989 | Shinada ...................... 348/625 |
| 4,935,612 A | | 6/1990 | Bierleutgeb |
| 5,192,998 A | * | 3/1993 | Tokumitsu et al. ......... 348/349 |
| 5,212,516 A | * | 5/1993 | Yamada et al. ............. 348/354 |
| 5,440,340 A | * | 8/1995 | Tsurutani et al. ........... 348/190 |
| 5,573,492 A | | 11/1996 | Dianna et al. |
| 5,648,652 A | | 7/1997 | Sekiya et al. |
| 6,157,783 A | | 12/2000 | Ide |

OTHER PUBLICATIONS

Patent Abstracts of Japan, Publication No. 09253041, Publication Date Sep. 30, 1997, Title: Endoscope System.

* cited by examiner

*Primary Examiner*—John P. Leubecker
(74) *Attorney, Agent, or Firm*—Fish & Richardson, P.C.

(57) ABSTRACT

An endoscopic apparatus and method allow for robust autofocusing operation regardless of contrast characteristics of the environment. The endoscopic apparatus and method can focus on a field stop edge and store default information of the apparatus focused on the edge. Later, if the endoscope fails to focus on an internal target object during the course of normal operation, the endoscope recalls the default information from memory to focus the lens on the edge of the field stop. Thus, internal structural objects in front of the endoscopic apparatus are brought into reasonable focus for visualization.

16 Claims, 6 Drawing Sheets

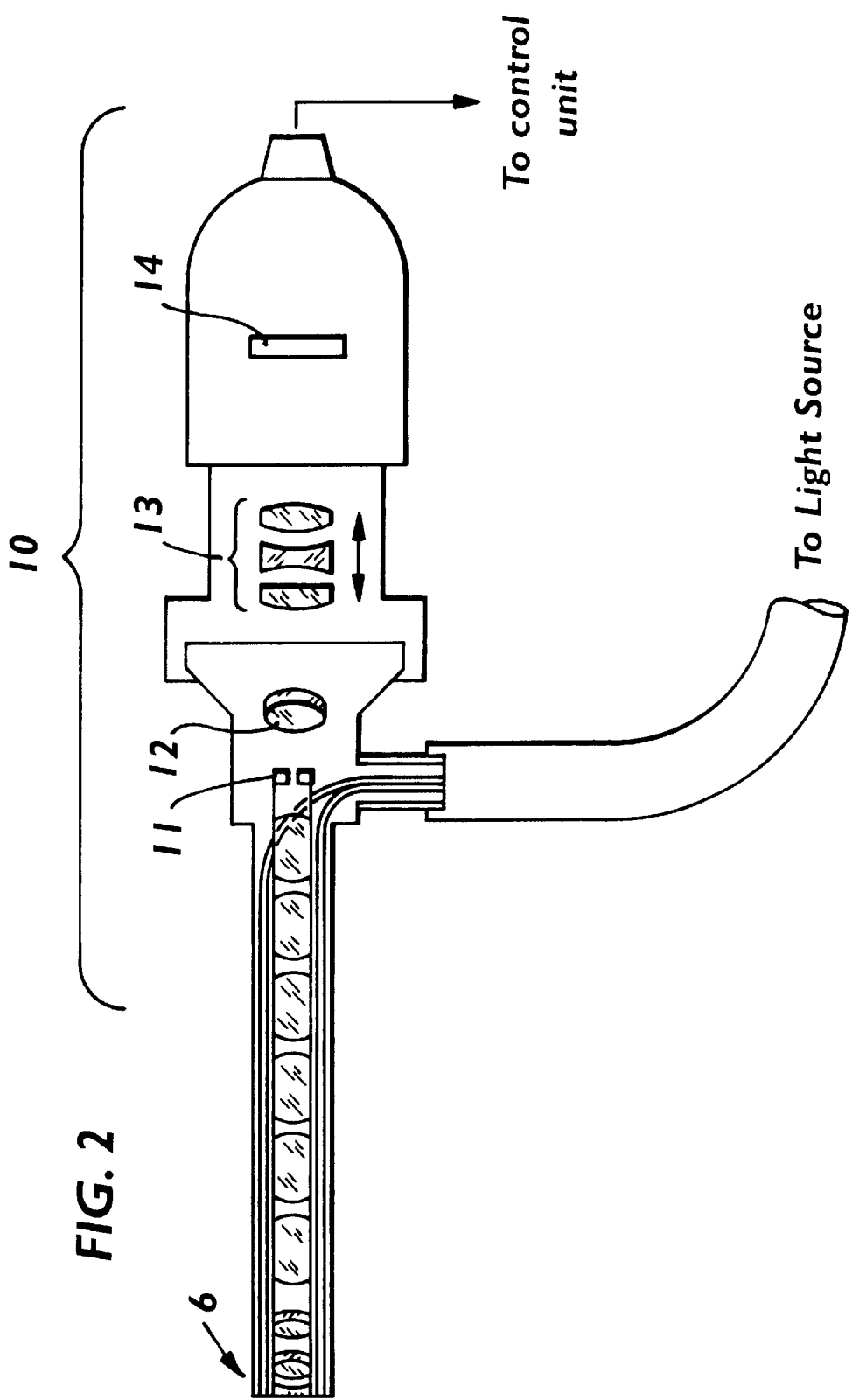

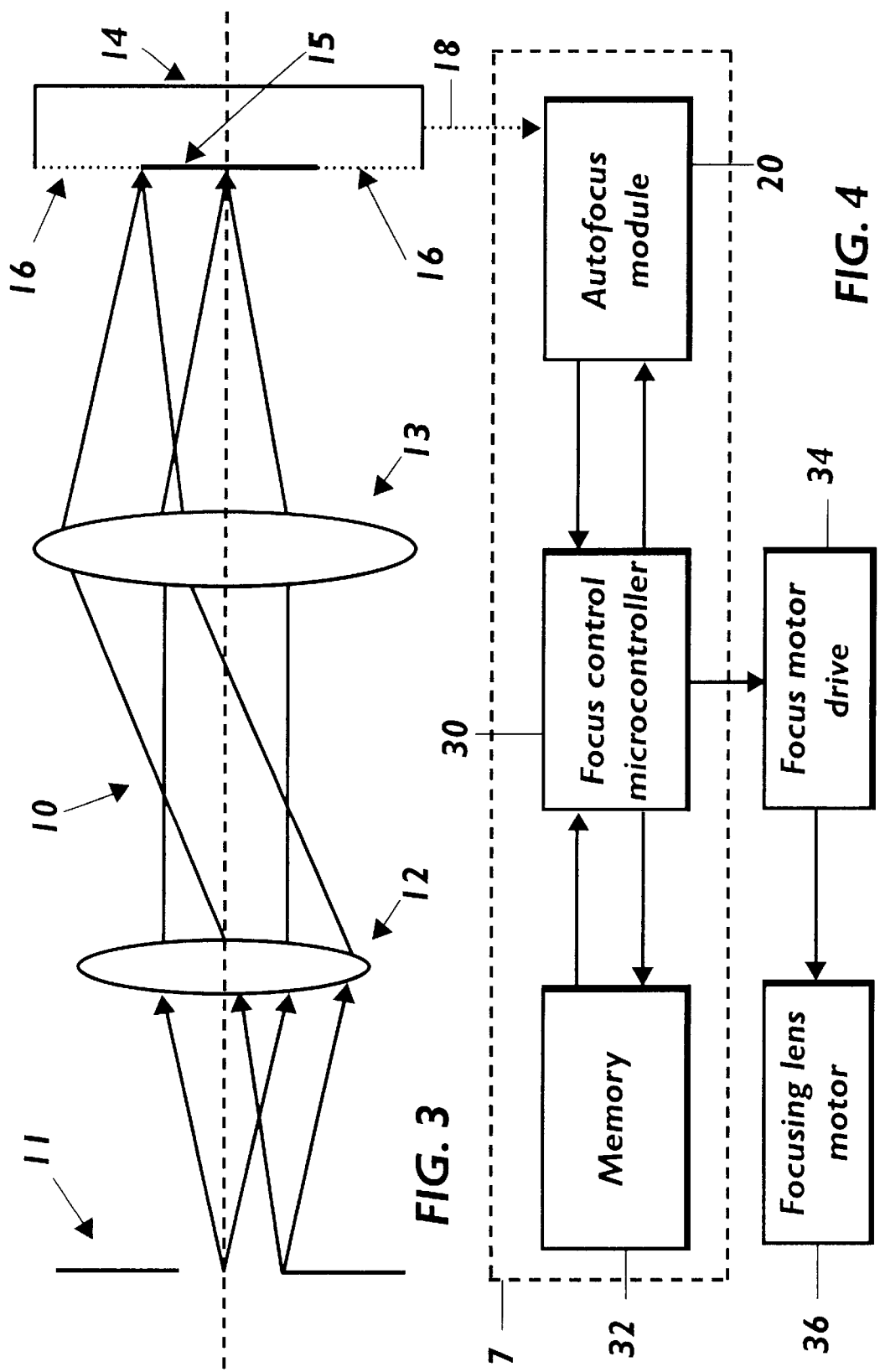

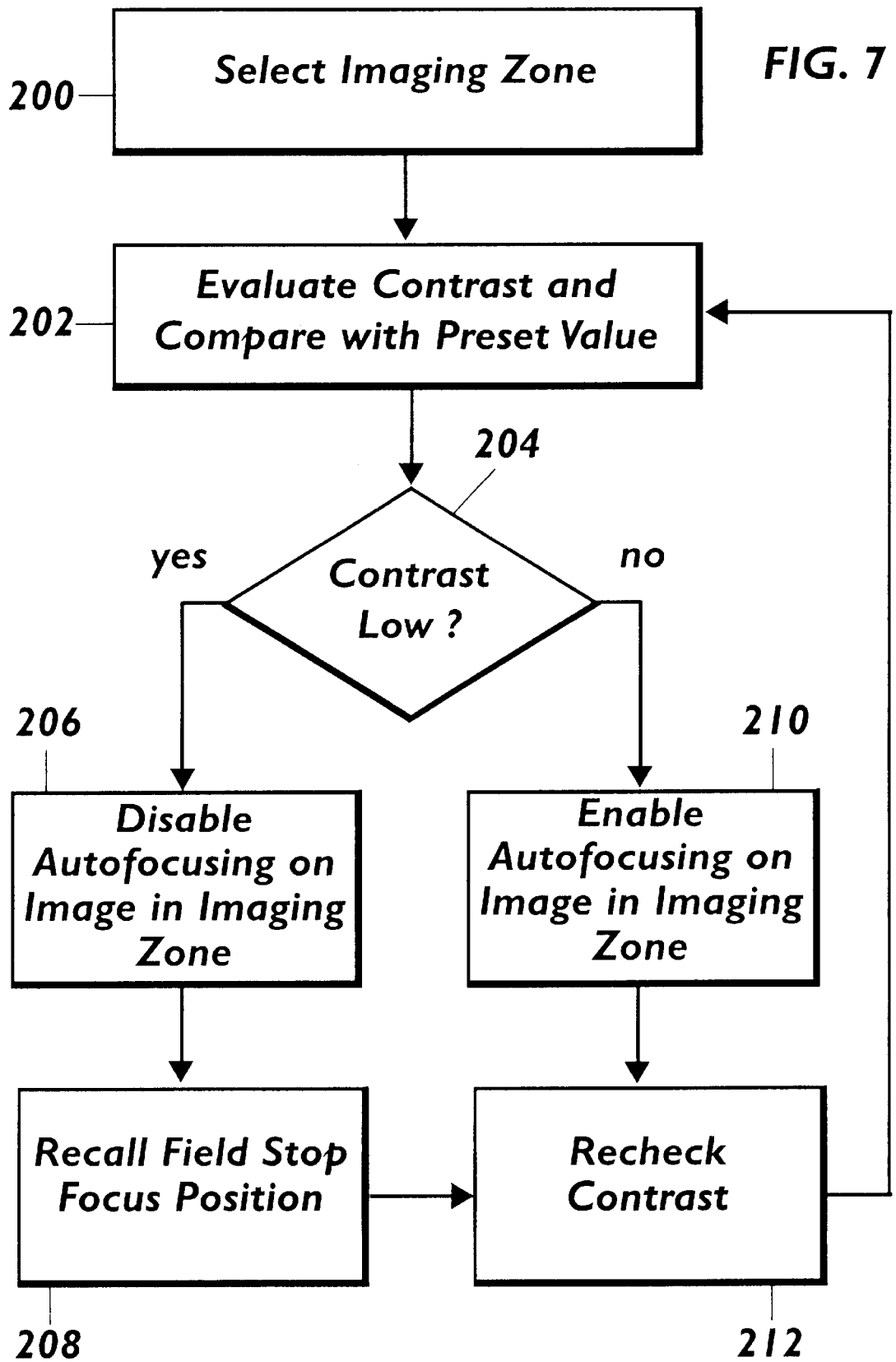

AUTOFOCUSING ENDOSCOPIC SYSTEM

BACKGROUND OF THE INVENTION

Autofocusing cameras typically use edge and contrast detection methods to autofocus on objects. Among others, Ide (U.S. Pat. No. 6,157,783), Nishida (U.S. Pat. No. 5,710, 662), Koyanage et al. (U.S. Pat. No. 5,352,882, and Kaneda (U.S. Pat. No. 5,027,147), all incorporated by reference, discuss the edge and contrast detection methods. If the contrast detection methods of autofocusing cameras are applied to endoscopic systems, such systems may have difficulties focusing on an object at a target site under harsh conditions. For example, a fogged body cavity environment, fumes from electrosurgery or laser surgery or a low contrast content of the field of view in general can prevent appropriate autofocusing on the internal target object. The situation is aggravated by relatively large depths of focus of endoscopes, especially of small diameter scopes. Thus, generally, an operator of an endoscopic system focus on the internal target object manually.

SUMMARY OF THE INVENTION

An apparatus and method according to the present invention allows for robust autofocusing operation regardless of contrast characteristics of the environment.

One aspect of the invention is a method for maintaining a focused image viewed by an autofocusing endoscope having an optical system including determining an transition between an imaging area and a non-imaging area, focusing the optical system on the transition, and storing in a memory a position of the optical system focused on the edge.

Embodiments of this aspect of the invention may include one or more of the following features. The method includes selecting at least a portion of the imaging area for focusing, determining a contrast value of at least the portion of the imaging area, comparing the contrast value of at least the portion of the imaging area with a preset value, moving the optical system to the position of the optical system stored in the memory to focus on the edge if the contrast value is below the preset value, and focusing the optical system on at least the portion of the imaging area if the contrast value is above the preset value. The contrast within the focusing zone can be checked at a predetermined frequency.

In another aspect of the invention, an article including a machine-readable medium that stores machine-executable instructions causes an endoscopic apparatus to determine an transition between an imaging area and a non-imaging area, focus the optical system on the transition, and store in a memory a position of the optical system focused on the edge.

The article can further cause the endoscopic apparatus to select at least a portion of the imaging area for focusing, determine a contrast value of at least the portion of the imaging area, compare the contrast value of at least the portion of the imaging area with a preset value, move the optical system to the position of the optical system stored in the memory to focus on the edge if the contrast value is below the preset value, and focus the optical system on at least the portion of the imaging area if the contrast value is above the preset value. The article can further cause the endoscopic apparatus to check the contrast within the focusing zone at a predetermined frequency.

In still another aspect of the invention, an endoscopic apparatus includes an optical system, an autofocusing module for focusing the optical system on a selected focusing zone, and a memory component for storing a position of the optical system focused on the edge. The selected focusing zone includes a zone around an edge between an imaging area and a non-imaging area. The autofocusing module includes an image size detector for finding the edge between the imaging area and the non-imaging area, a zone selector for selecting the focusing zone including the zone around the edge, and an edge detector for focusing the optical system on the edge.

The endoscopic apparatus can further include a driver for moving the optical system and a focus controller for controlling the driver. The focus controller can interact with the autofocusing module to focus the optical system on the edge.

Also, the endoscopic apparatus can include a photosensitive device for converting an image transmitted from the optical system into video signals. The video signals are transmitted to the autofocusing module for signal processing.

Among other advantages, the endoscopic apparatus and method of the present invention allow the optical system to focus on a field stop edge—the edge of a field of view—and store default information of the apparatus focused on the edge. Later, if the apparatus fails to focus on an internal object during the course of normal operation, the apparatus recalls the default information from memory to focus the lens on the field stop edge. In the present invention, manual focusing is obviated. Thus, objects in front of the endoscopic apparatus are brought into reasonable focus for visualization automatically.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 2 illustrates an optical system of an endoscopic apparatus in accordance with the present invention.

FIG. 3 illustrates an enlarged section of the optical system of FIG. 2.

FIG. 4 shows a control unit of an endoscopic apparatus in accordance with the present invention.

FIG. 7 shows steps for autofocusing on a field stop edge according to an embodiment of the present invention.

DETAILED DESCRIPTION OF PREFERRED EMBODIMENTS

Figure 1:
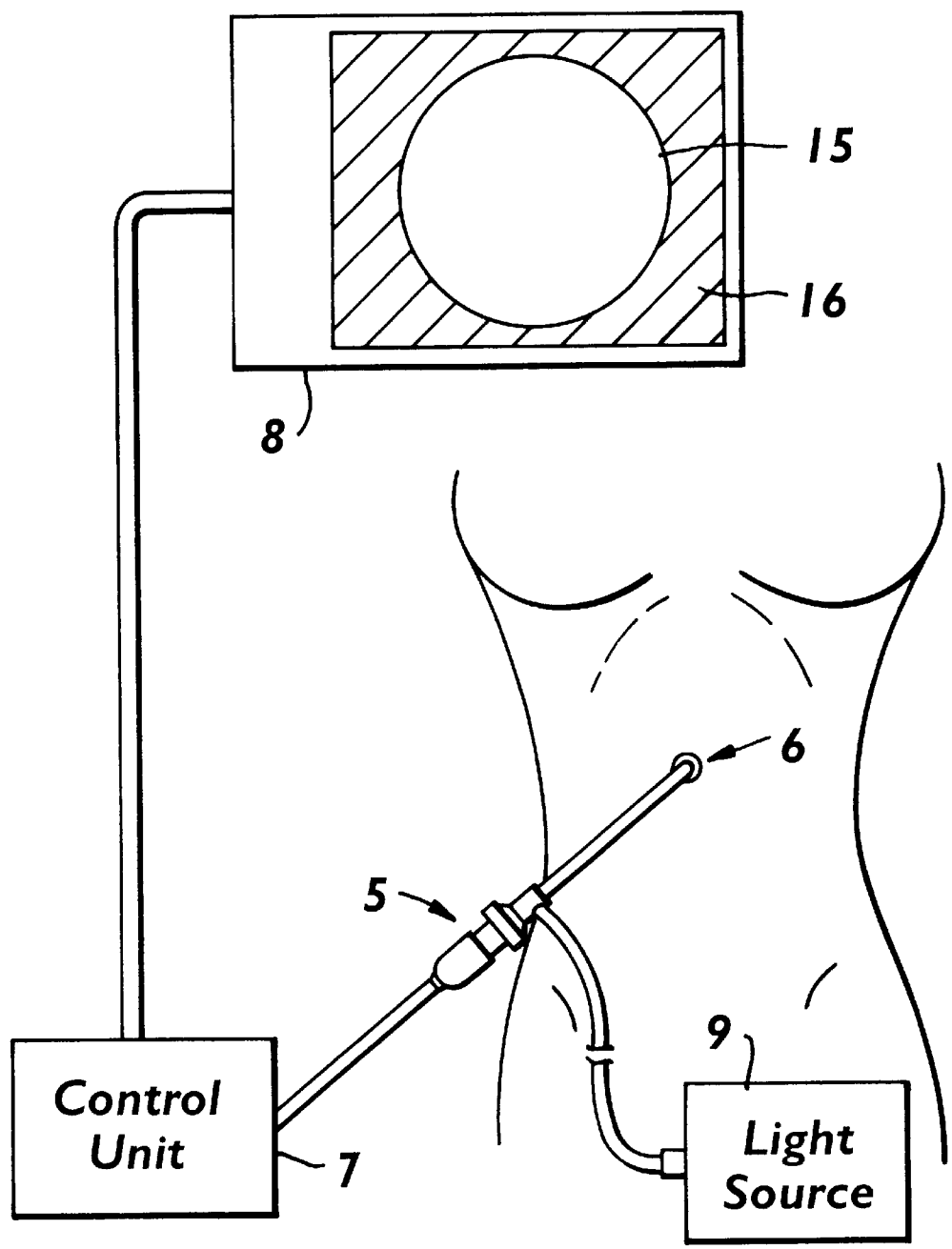
FIG. 1 illustrates one embodiment of an endoscopic apparatus in accordance with the present invention.

FIG. 1 shows an endoscopic system 5 according to an embodiment of the present invention. An optical end 6 of the endoscopic system 5 is inserted into the body, and video signals from the optical end 6 is transmitted to a control unit 7, which processes the signals to show internal structures on a video monitor 8. A light source 9 is provided to the endoscopic system 5.

Referring to FIG. 2, the optical end 6 leads to an optical system 10, having a field stop 11, an ocular lens 12, a coupler lens 13, and a photosensitive imaging device 14, such as a CCD or CMOS imager. An object under examination is visualized through the field of view of the field stop 11.

Referring to FIG. 3, the ocular lens 12 of the optical system 10 forms a virtual image of the object in the field of the view defined by the field stop 11; and the coupler lens 13 projects the virtual image formed by the lens 12 to the photosensitive imaging device 14. The coupler lens 13 is shown schematically as one single lens for illustration purposes only. The lens 13 may actually be a complex lens assembly of fixed lenses and movable lenses for zooming and focusing on a target. In a variation of the system, the ocular lens 12 may be omitted and the virtual image may be projected directly on the imaging device 14 by the coupler lens 13.

A projected image on the imaging device 14 is called a real image. The projected real image includes an effective imaging area 15 (the bold line) and a non-imaging black area 16 (the dashed line). The video monitor 8 of FIG. 1 illustrates the imaging area 15 and the black area 16.

Referring to FIG. 4, the control unit 7 includes an autofocus module 20, a focus control microcontroller 30, and a memory 32. The focus control microcontroller 30 is coupled to the autofocus module 20, and a memory 32 is connected to the microcontroller 30. A focus motor drive 34 is coupled to the microcontroller 30 for driving a focusing lens motor 36, which moves a lens for focusing. The lens moved for focusing may be the coupler lens 13 or the ocular lens 12 or both.

When the endoscopic system 5 is initialized optionally by the user or automatically during the initial system boot-up, a video output signal 18 from the imaging device 14 is fed to the autofocus module 20. The video signal 18 is processed by the autofocus module 20 to find the edge of the field stop 11 (the function of the autofocus module 20 is discussed in greater detail later). Then, to focus on the edge of the field stop 11, the focus control microcontroller 30 interacts dynamically with the autofocus module 20 and activates the focus motor drive 32, which drives the focusing lens motor 36 to focus the coupler lens 13 or the ocular lens 12 or both on the edge of the field stop 11. The lens position focused on the edge of the field stop 11 (field stop focus position) is stored in the memory 32. Thus, whenever an object projected to the effective imaging area 15 cannot be focused, a default setting of the field stop focus position stored in the memory 32 during system initialization is recalled to provide a reasonable visualization of the object.

Figure 5:
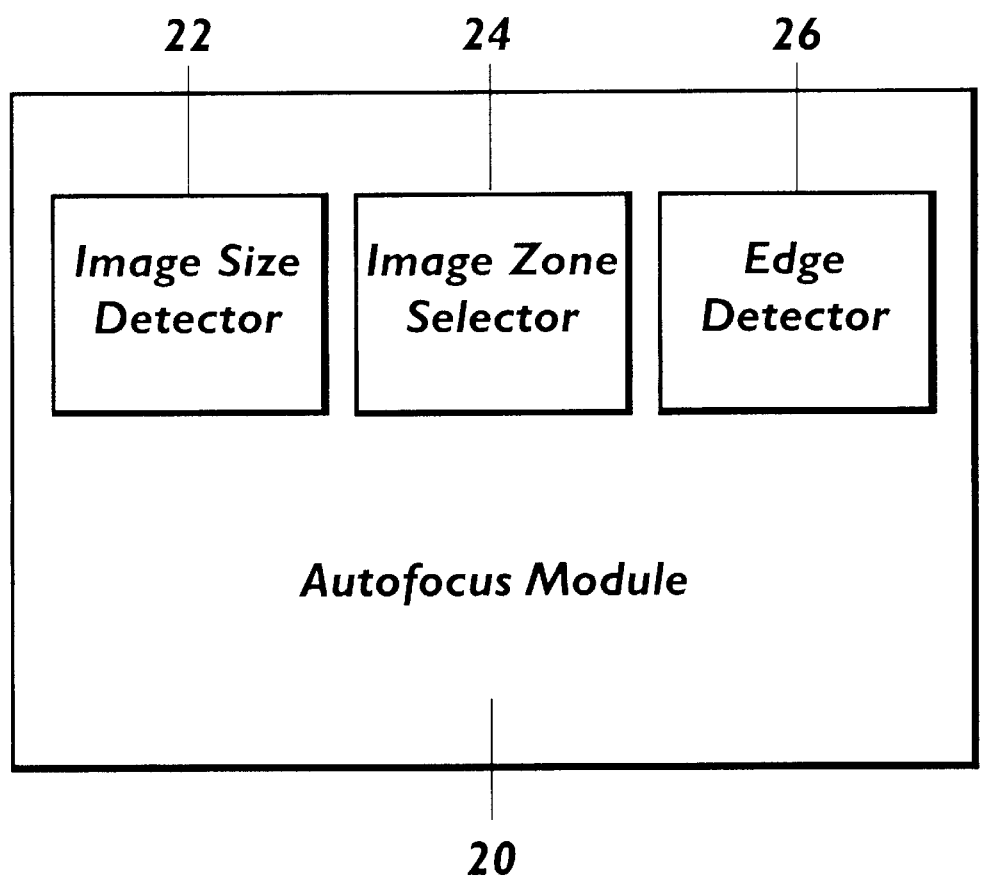
FIG. 5 illustrates an autofocus module according to an embodiment of the present invention.

Referring to FIG. 5, to find the edge of the field stop 11 in the video signal and to focus on the edge, the autofocus module 20 has at least the following circuit components: an image size detector 22, an image zone selector 24, and an edge detector 26. The components of the autofocus module 20 operate as follows.

Figure 6:
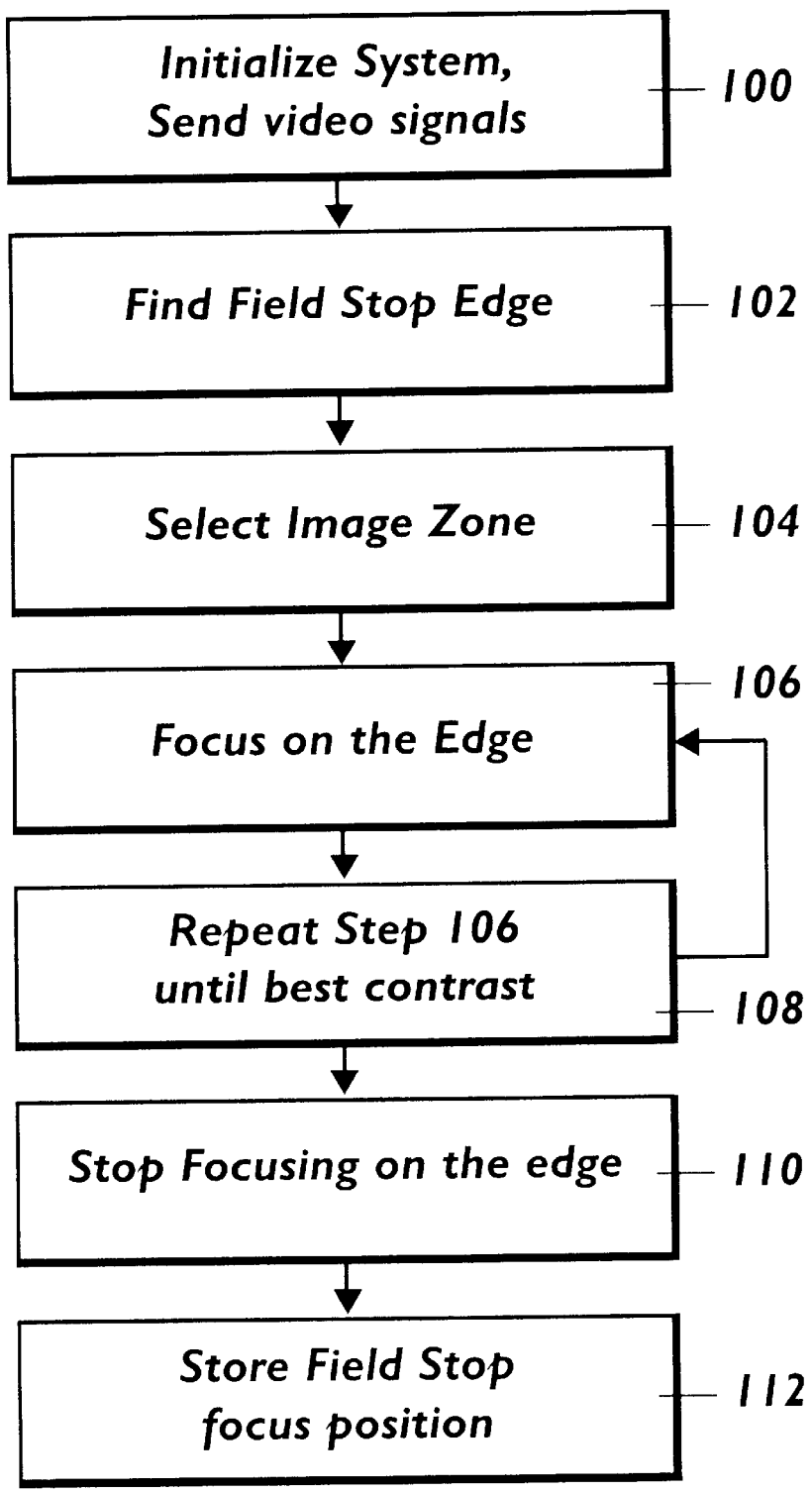
FIG. 6 shows steps for storing autofocus information of a field stop edge according to an embodiment of the present invention.

Referring to FIG. 6, after the endoscopic system 5 is initialized, a video signal 18 is sent from the imaging device 14 to the autofocus module 20 for image processing (Step 100). The image size detector 24 finds an edge of the field stop within the video signal image (Step 102). The image size detector 24 does this by, for example, digitally filtering the high frequencies of the video signal 18 to extract out the edge component.

Then, the image zone selector 24 selects an image zone around the field stop edge (Step 104). The microcontroller 30 then controls the focus motor drive 34 to send signals to the focusing lens motor 36 to focus the coupler lens 13 on the field stop edge in the image zone (Step 106).

The contrast of the field stop edge is generally high because the edge represents a transition from the imaging area 15 to the black area 16. Step 106 is repeated until the edge detector 26 detects the highest and the sharpest contrast, that is, the highest focalization, of the field stop edge (Step 108). A degree of focalization is related to a high frequency content of a signal. Therefore, the edge detector 26 detects a degree of focalization by, for example, evaluating the high frequency content of the signal.

The autofocus module 20 then sends a signal to the microcontroller 30 to stop the motor 36 (Step 110). Then, the information of the field stop focus position is stored in the memory 32 (Step 112).

After the field stop focus position is stored in the memory 32, the steps as shown in FIG. 7 are executed. An imaging zone, generally set at the center of the imaging area 15, is selected by the image zone selector 24 for autofocusing (Step 200). The edge detector 26 then evaluates the contrast and compares it with a preset minimum value (Step 202). If the contrast is determined to be low relative to a preset value (step 204), then the autofocusing of the image in the imaging zone is stopped (Step 206), and the default field stop focus position is recalled from the memory 32 (Step 208). If the contrast is determined to be above a preset value (Step 204), then the autofocusing is enabled (Step 210). From either Step 208 or 210, the contrast can be rechecked periodically, for example, every 2 seconds, by going back to Step 202 to constantly monitor and update the visual field (Step 212).

The foregoing technique can be implemented on a machine executable program. The program can be stored on a storage medium such as random access memory (RAM) and read by a programmable machine incorporated in the endoscopic system 5.

A number of embodiments of the invention have been described. Nevertheless, it will be understood that various modifications may be made without departing from the spirit and scope of the invention. Accordingly, other embodiments are within the scope of the following claims.

What is claimed is:

1. A method for maintaining a focused image viewed by an autofocusing endoscopic apparatus having an optical system, the method comprising:
   determining a transition between an imaging area and a non-imaging area;
   focusing the optical system on the transition; and
   storing in a memory a position of the optical system focused on the transition.

2. The method according to claim 1 further comprising:
   selecting at least a portion of the imaging area for focusing;
   determining a contrast value of at least the portion of the imaging area;
   comparing the contrast value of at least the portion of the imaging area with a preset value; and
   moving the optical system to the position of the optical system stored in the memory to focus on the transition if the contrast value is below the preset value.

3. The method according to claim 2, further comprising:
   determining and comparing the contrast value at a predetermined frequency.

4. The method according to claim 1 further comprising:
   selecting at least a portion of the imaging area for focusing;
   determining a contrast value of at least the portion of the imaging area;

comparing the contrast value of at least the portion of the imaging area with a preset value; and focusing the optical system on at least the portion of the imaging area if the contrast value is above the preset value.

5. The method according to claim 4 further comprising:

determining and comparing the contrast value at a predetermined frequency.

6. An method maintaining a focused image viewed by an autofocusing endoscopic apparatus having an optical system, the method comprising:

determining a transition between an imaging area and a non-imaging area;

focusing the optical system on the transition; and storing in a memory a position of the optical system focused on the transition;

selecting at least a portion of the imaging area for focusing;

determining a contrast value of at least the portion of the imaging area;

comparing the contrast value of at least the portion of the imaging area with a preset value;

moving the optical system to the position of the optical system stored in the memory to focus on the transition if the contrast value is below the preset value; and focusing the optical system on at least the portion of the imaging area if the contrast value is above the preset value.

7. An article comprising a machine-readable medium that stores machine-executable instructions for causing an endoscopic apparatus to:

determine an transition between an imaging area and a non-imaging area;

focus the optical system on the transition; and store in a memory a position of the optical system focused on the transition.

8. The article according to claim 7 further including instruction for causing the endoscopic apparatus to:

select at least a portion of the imaging area for focusing;

determine a contrast value of at least the portion of the imaging area;

compare the contrast value of at least the portion of the imaging area with a preset value; and move the optical system to the position of the optical system stored in the memory to focus on the transition if the contrast value is below the preset value.

9. The article according to claim 8 further including instruction for causing the apparatus to determine and compare the contrast value at a predetermined frequency.

10. The article according to claim 7 further including instruction for causing the apparatus to:

select at least a portion of the imaging area for focusing;

determine a contrast value of at least the portion of the imaging area;

compare the contrast value of at least the portion of the imaging area with a preset value; and focus the optical system on at least the portion of the imaging area if the contrast value is above the preset value.

11. The article according to claim 10 further including instruction for causing the apparatus to determine and compare the contrast value at a predetermined frequency.

12. An endoscopic apparatus comprising:

an optical system;

an autofocusing module for focusing the optical system on a selected focusing zone; the selected focusing zone including a zone around an edge between an imaging area and a non-imaging area and;

a memory for storing a position of the optical system focused on the edge.

13. The endoscopic apparatus according to claim 12 wherein the autofocusing module comprises:

an image size detector to find the edge between the imaging area and the non-imaging area;

a zone selector to select the focusing zone including the zone around the edge; and an edge detector to focus the optical system on the edge.

14. The endoscopic apparatus according to claim 12 further comprising:

a driver for moving focusing elements of the optical system; and a focus controller for controlling the driver;

wherein the focus controller interacts with the autofocusing module to focus the optical system on the edge.

15. The endoscopic apparatus according to claim 12 further comprising:

a photosensitive device for converting an image transmitted from the optical system into video signals, wherein the video signals are transmitted to the autofocusing module for signal processing.

16. The endoscopic apparatus according to claim 14, wherein the focusing elements comprise movable lenses.

* * * * *